United States Patent
Steinbauer et al.

(10) Patent No.: US 6,518,455 B1
(45) Date of Patent: Feb. 11, 2003

(54) PROCESS FOR PREPARING SUBSTITUTED AROMATIC AND HETEROAROMATIC ALDEHYDES AND CARBOXYLIC ACIDS

(75) Inventors: Gerhard Steinbauer, Enns (AT); Karlheinz Giselbrecht, Pasching (AT); Manfred Schöftner, Linz (AT); Klaus Reiter, Linz (AT)

(73) Assignee: DSM Fine Chemicals Austria Nfg GmbH & CoKG, Linz (AT)

(*) Notice: Subject to any disclaimer, the term of this patent is extended or adjusted under 35 U.S.C. 154(b) by 0 days.

(21) Appl. No.: 09/473,020

(22) Filed: Dec. 28, 1999

(30) Foreign Application Priority Data

Dec. 28, 1998 (AT) ............................................... 2174/98
Apr. 28, 1999 (AT) ............................................... 748/99

(51) Int. Cl.⁷ ...................... C07C 309/00; C07C 51/255
(52) U.S. Cl. ............................ 562/51; 562/408; 562/409
(58) Field of Search ............................ 562/469, 51, 408

(56) References Cited

U.S. PATENT DOCUMENTS

| | | | |
|---|---|---|---|
| 3,799,940 A | 3/1974 | Mains | 260/340.5 |
| 3,978,119 A | * 8/1976 | Onopchenko et al. | 260/523 |
| 6,127,572 A | * 10/2000 | Ford | |

FOREIGN PATENT DOCUMENTS

| | | | |
|---|---|---|---|
| DE | 115410 | * 11/1900 | |
| DE | 1 271 713 | 5/1966 | |
| ES | 2041214 | * 11/1993 | C07C/205/44 |

OTHER PUBLICATIONS

Alexander McKillop et al, "Further Functional Group Oxidations Using Sodium Perborate", Tet., vol. 45 (1989), pp. 3299–3306.*

Stephen O. Nwaukwa et al, "The Oxidation of Aldehydes to Acods with Calcium Hypochlorite", Tet. Lett., vol. 23 (1982), pp. 3131–3134.*

Paul Ruggli et al, "Über o,o'–Disulfosäuren der Stilben– und Tolanreihe II", Helv. Chim. Acta, vol. 15 (1932), pp. 576–590.*

Lange et al, Trace–level determination of aromatic sulfonates in water by online ion–pair extraction/ion–pair chromatography and their behavior in the aquatic environment, 1995, Journal of High Resolution Chromatography, 18(4), 243–52, Abstract.*

Long, The Ozonization Reaction, 1940, Chemical Reviews, 27, pp. 437–493.*

Patent Abstracts of Japan, No. 08–003138 (1999).
Chemical Abstracts, 110(4), 25750x (1989).
Chemical Abstracts, 78(9), 57884f (1973).

* cited by examiner

Primary Examiner—James O. Wilson
Assistant Examiner—Paul A. Zucker
(74) Attorney, Agent, or Firm—Wenderoth, Lind & Ponack, L.L.P.

(57) ABSTRACT

A process for preparing substituted aromatic and heteroaromatic aldehydes or carboxylic acids of the formula

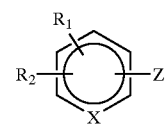

I in which $R_1$ and $R_2$ are H, $C_1$–$C_4$ alkyl, $C_1$–$C_4$ alkoxy, OH, $NO_2$, CN, COOH, $CONH_2$, COOR, $NH_2$, $SO_3H$ or halogen and R is $C_1$–$C_4$ alkyl and where $R_1$ and $R_2$ are not simultaneously H, X is C or N and Z is CHO or COOH, from the corresponding symmetric stilbene compounds of the formula

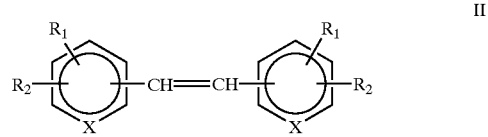

II in which $R_1$, $R_2$ and X are as defined above, by aqueous ozonolysis and subsequent isolation of an aldehyde or oxidation to give the corresponding carboxylic acid.

9 Claims, No Drawings

PROCESS FOR PREPARING SUBSTITUTED AROMATIC AND HETEROAROMATIC ALDEHYDES AND CARBOXYLIC ACIDS

Aromatic and heteroaromatic aldehydes and carboxylic acids, such as 4-nitro-2-sulfobenzaldehyde or -benzoic acid, are intermediates in the preparation of herbicides and plant growth regulators.

DE 42 36 902 describes the preparation of 4-nitro-2-sulfobenzoic acid via $KMnO_4$ oxidation of 4-nitrotoluene-2-sulfonic acid. However, this route is not suitable for an environmentally friendly large-scale industrial preparation of the desired compound. This is also true for other known oxidation methods, for example those involving sodium hypochlorite and nickel peroxide. Helv. Chimica Acta 15, 576, 583 (1932) discloses the use of 4,4'-dinitrostilbene-2,2'-disulfonic acid as starting material. However, once more the oxidation is carried out using $KMnO_4$.

For this reason, novel synthesis routes for preparing aromatic and heteroaromatic carboxylic acids and aldehydes are investigated by which routes the desired end products can be prepared in an environmentally friendly manner even on a large industrial scale.

Accordingly, the present invention provides a process for preparing substituted aromatic and heteroaromatic aldehydes or carboxylic acids of the formula

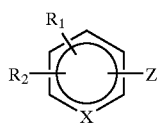

I in which $R_1$ and $R_2$ are H, $C_1$–$C_4$ alkyl, $C_1$–$C_4$ alkoxy, OH, $NO_2$, CN, COOH, $CONH_2$, COOR, $NH_2$, $SO_3H$ or halogen and R is $C_1$–$C_4$ alkyl and where $R_1$ and $R_2$ are not simultaneously H, X is C or N and Z is CHO or COOH, which comprises dissolving a corresponding symmetric stilbene compound of the formula

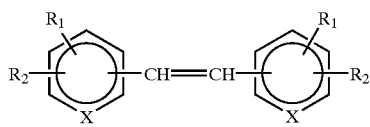

II in which $R_1$, $R_2$ and X are as defined above either directly or as a salt in water and reacting it at a temperature of from 0 to +100° C. with ozone, giving a mixture comprising the corresponding aldehyde of the formula I and hydroperoxide from which a) after acidic or alkaline decomposition of the hydroperoxide, the corresponding aldehyde of the formula I is isolated, or which b) is directly reacted, under acidic or alkaline decomposition of the hydroperoxide and with addition of an oxidizing agent, to give the corresponding carboxylic acid of the formula I or its salt, which is then isolated.

The process according to the invention is suitable for preparing compounds of the formula I.

These compounds can be aromatic or heteroaromatic aldehydes or carboxylic acids. Accordingly, the substituent Z is CHO or COOH. In the o, m or p position to this substituent, a C atom of the aromatic ring can be replaced by an N atom, so that X can be C or N. The ring furthermore carries the substituents $R_1$ and $R_2$, which can likewise be positioned in the o, m or p position to Z. If one of these positions is replaced by X=N, the N atom does not have any substituents.

In the formula I, $R_1$ and $R_2$ are H, $C_1$–$C_4$ alkyl, $C_1$–$C_4$ alkoxy, OH, $NO_2$, CN, COOH, $CONH_2$, $NH_2$, COOR, $SO_3H$ or halogen, such as Cl, Br, F.

R can be $C_1$–$C_4$ alkyl. However, $R_1$ and $R_2$ may not simultaneously be H. $R_1$ is preferably $NO_2$ and $R_2$ is preferably $SO_3H$.

Thus, examples of the compounds which can be prepared by the process according to the invention are 2-sulfobenzoic acid, 4-nitro-2-sulfobenzoic acid, 4-nitro-2-sulfobenzaldehyde, 4-aminobenzoic acid, terephthalic acid, substituted pyridine carboxylic acids, such as 2,3-pyridinedicarboxylic acid, etc., or their Na or K salts.

Preference is given to preparing 4-nitro-2-sulfobenzaldehyde or -benzoic acid, or the Na or K salt of 4-nitro-2-sulfobenzoic acid.

The starting materials used are the corresponding symmetric stilbene compounds of the formula II in which the substituents $R_1$ and $R_2$ are as defined for the compounds of the formula I.

Furthermore, if heteroaromatic end products are to be prepared, in each case one C atom in the rings is replaced by an N atom.

Suitable compounds of the formula II are employed directly or in the form of their salts.

Suitable salts are, for example, Na or K salts of acids or chlorides, nitrates, sulfates, phosphates of basic groups.

Examples of suitable starting materials are, accordingly, stilbenes such as stilbene-2,2'-disulfonic acid, 4,4'-dinitrostilbene-2,2'-disulfonic acid, 4,4'-vinylenedianiline, 4,4'-vinylenedipyridine, 4,4'-stilbenedicarboxylic acid, etc., or salts of these compounds.

The starting materials are dissolved in such an amount of water that a 1–50% strength, preferably a 5–15% strength, solution is obtained.

If the starting material itself is not water-soluble, an aqueous solution of the corresponding salt can be prepared by adding suitable bases or acids.

The resulting solution is treated with a gaseous ozone-carrying $O_2$ stream sufficiently long for the equivalent amount of ozone or an excess to be taken up.

The end and thus the duration of the reaction is defined by the consumption of the theoretical amount of ozone and can easily be determined by a simultaneously occurring increased ozone breakthrough.

The end of the reaction can furthermore easily be determined by suitable in-process monitoring of the consumption of the starting material.

The temperature of the ozonolysis is from 0 to 100° C. Preference is given to a temperature of from +5 to +80° C., particularly preferably from +15 to +70° C.

After the ozonolysis has ended, the mixture comprises equimolar amounts of the corresponding aldehyde of the formula I and the corresponding hydroperoxide.

The hydroperoxide is then subjected to acidic or alkaline decomposition. Accordingly, the reaction mixture is, after the ozonolysis, heated in aqueous acidic solution, or an aqueous solution of a base is added until no more peroxide can be detected in the reaction mixture.

After the decomposition, the hydroperoxide can give rise either to the corresponding acid or to the aldehyde.

If the aldehyde is the desired end product, it is isolated from the mixture. The formation of aldehyde or acid from the hydroperoxide depends on the substituents of the compound of the formula I.

Preference is given to isolating an aldehyde of the formula I which, as substituent $R_1$, has $NO_2$ and, as substituent $R_2$, has H or $SO_3H$.

To isolate the aldehyde, the hydroperoxide is preferably subjected to an alkaline decomposition. To this end, particular preference is given to using aqueous sodium hydroxide solution, which is added until an alkaline pH, preferably of more than pH 8, is reached.

The mixture is then cooled and the aldehyde is crystallized out.

If the desired end product is the corresponding carboxylic acid, an oxidizing agent is immediately, without isolation of the aldehyde, added to the reaction mixture which is obtained after the ozonolysis and which comprises aldehyde and hydroperoxide compound.

Suitable oxidizing agents are, for example, hydrogen peroxide, peracids, ozone, molecular oxygen, sodium hypochlorite or sodium perborate. Preference is given to using hydrogen peroxide or a peracid. The oxidizing agent is added in an amount which is at least equimolar to the amount of aldehyde present in the reaction mixture, i.e. in an amount which is at least 0.5 molar, based on the stilbene employed. The temperature of the oxidation varies depending on the oxidizing agent used and is in a temperature range of from 0 to 100° C.

The acidic or basic decomposition of the hydroperoxide can be carried out either before or after the oxidation, but also at the same time as the oxidation. Preference is given to subjecting the hydroperoxide to acid decomposition.

After the oxidation has ended, the corresponding carboxylic acid or its salt, preferably the Na or K salt, is crystallized, for example either directly by crystallization from the aqueous reaction mixture, for example by concentration, cooling or addition of a suitable precipitating agent, or first extracted with an organic solvent, followed by crystallization of the target product from the extract.

If the starting material used is the sodium salt of the corresponding compound and if the desired end product is the K salt of the carboxylic acid, this is precipitated, for example, by addition of potassium salts, such as potassium chloride, aqueous potassium hydroxide solution, potassium formate, potassium acetate, potassium carbonate, etc.

The mother liquor which is obtained when the reaction mixture is worked up can, after concentration, be recycled into a new oxidation batch. This is advantageous, in particular, if the peroxide decomposition is carried out using acetic acid, since, together with the mother liquor, the acetic acid is recycled, too.

The process according to the invention affords the desired aldehydes and carboxylic acids, if appropriate in the form of their salts, in an environmentally friendly way, since hardly any waste is produced owing to the use of symmetric stilbenes as starting material.

The target products can be obtained in high purity and in high yields.

The process according to the invention is particularly suitable for preparing 4-nitro-2-sulfobenzaldehyde or -benzoic acid or the sodium or potassium salt of this compound.

EXAMPLE 1

At 30° C., a stream of oxygen which contained 50 g/m³ of ozone was introduced at a rate of 100 liter/hour into a solution of 5.2 g of 4,4'-dinitrostilbene-2,2'-disulfonic acid disodium salt in 70 ml of water. After 8 minutes, the uptake of ozone had ended.

4N NaOH was then added until a constant pH of 9.5 had been reached. A peroxide test showed that there was virtually no peroxide left in the solution.

The solution was cooled to 5° C. and the product that had crystallized out was filtered off with suction and washed with a little 5° C.-cold water.

The mother liquor was concentrated under reduced pressure to a volume of 30 ml and once more cooled to 5° C., and the crystalline product was filtered off with suction, washed with cold water and combined with the first batch of crystals. Drying under reduced pressure gave 4.7 g of 4-nitro-2-sulfobenzaldehyde, sodium salt (85% of theory). The product is present as the monohydrate.

The structure was confirmed by $^1$H NMR, $^{13}$C NMR, IR and elemental analysis. $^1$H NMR: δ=10.9 ppm (1H; —CHO), 8.5 ppm (1H; Ar—H), 8.3 (1H; d, J=8 Hz, Ar—H), 8.0 (1H; d, J=8 Hz, Ar—H)

$^{13}$C NMR: δ=194 ppm (—CHO), 153/151/139/131/126/124 (6Ar—C)

Elemental analysis: $C_7H_6NO_7SNa.H_2O$ (271.18) calc. C 31.0%; H 2.2%; N 5.2%; Na 8.5%, $H_2$ 6.6% found C 31.2%; H 2.2%; N 5.2%, Na 8.5%, $H_2$ 6.9%

EXAMPLE 2

At 33° C., a stream of oxygen which contained 45 g/m³ of ozone was introduced into a solution of 300 g (0.414 mol) of 4,4'-dinitrostilbene-2,2'disulfonic acid disodium salt in 3750 ml water. After 38 minutes, the uptake of ozone had ended.

This gave 400 ml of hydroperoxide (HPO) solution which contained 0.47 mol of hydroperoxide.

2000 ml of the resulting HPO solution were then initially charged and admixed with 200 ml of acetic acid, and 23.5 ml of 30% strength hydrogen peroxide were added dropwise. Over a period of one hour, the reaction solution was heated to 90° C., and from 85° C. onwards some gas was given off. After one hour at 90° C., the HPO content was 0.35 mol. In total, the reaction solution was kept at 90° C. for 13h, and during these 13 hours a 2nd portion of hydrogen peroxide (23.5 ml) and a portion of peracetic acid (0.207 mol) were added to the reaction mixture. The peroxide content decreased to 0.066 mol.

At a bath temperature of 60° C. and a pressure of 70 mbar, 1600 ml of water were then distilled off. The residue obtained was 600 ml of a clear solution having an HPO content of 0.04 mol. This solution was admixed with 33 g of sodium chloride, as a result of which a solid precipitated out, which was filtered off with suction. This gave 67.5 g (dry) of a solid which were recrystallized from 177 g of water and 354 g of acetic acid.

Yield 40 g of 4-nitro-2-sulfobenzoic acid sodium salt.

EXAMPLE 3

Similarly to Example 2, an HPO solution containing 0.44 mol of HPO was obtained, and 2100 ml (pH 2.9) of this solution were initially charged and admixed with 1000 ml of acetic acid (pH 1.7). 100 g of 30% strength hydrogen peroxide were then added, and the reaction mixture was heated to 80° C. over a period of one hour.

The reaction solution was kept at 80° C. for a total of 18h, and during these 18 hours two further portions of hydrogen peroxide (0.207 mol and 0.44 mol, respectively) were added to the reaction mixture. The peroxide content decreased to 0.10 mol.

Conc. sulfuric acid (72.7 g) was added to the resulting solution of pH 1.4 until a pH of 0.2 had been reached. 2000 ml were then distilled off at a bath temperature of 60° C. and a pressure of 90 mbar, after which crystallization started. The distillation residue was cooled to 15° C. and the precipitated solid was filtered off with suction.

Yield 99.4 g of 4-nitro-2-sulfobenzoic acid sodium salt.

1107 g of mother liquor were salted out using 75 g of sodium chloride, and the precipitated solid was filtered off with suction, giving a further 108.5 g of 4-nitro-2-sulfobenzoic acid sodium salt.

Melting point:>350° C.

NMR purity:>99%

EXAMPLE 4

Similarly to Example 2, an HPO solution which contained 0.60 mol of HPO was obtained, 1030 ml (0.30 mol of HPO; pH 2.6) of which were initially charged and admixed with 200 ml of formic acid. 66.6 g of 30% strength hydrogen peroxide were then added and the reaction mixture was heated to 80° C. over a period of one hour.

In total, the reaction solution was kept at 80° C. for 6h, and during these 6 hours two further portions of hydrogen peroxide (66.6 g each) were added to the reaction mixture. The peroxide content decreased to 0.052 mol.

At a bath temperature of 60° C. and a pressure of 90 mbar, 758 ml (801 g) were distilled off, and the distillation residue was then cooled under reduced pressure to 10° C. At an internal temperature of 35° C., crystallization started.

The solid was filtered-off with suction and dried, giving 34.9 g of 4-nitro-2-sulfobenzoic acid sodium salt (21.6% of theory, based on the stilbene employed).

532 g of mother liquor were salted out using 25 g of sodium chloride, and the precipitated solid was filtered off with suction, giving a total yield of 105 g of 4-nitro-2-sulfobenzoic acid sodium salt (65% of theory, based on the stilbene employed).

EXAMPLE 5

Similarly to Example 2, an HPO solution which contained 0.60 mol of HPO was obtained, 2000 ml (pH 2.6) of which were initially charged and admixed with 200 ml of formic acid. 132.2 g of 30% strength hydrogen peroxide were then added, and the reaction mixture was heated to 80° C. over a period of 45 min.

In total, the reaction solution was kept at 80° C. for 6h, and during these 6 hours, a further portion of hydrogen peroxide (132.2 g) was added to the reaction mixture.

At 80° C., 147.2 g (1.5 mol) of potassium acetate were added, and the mixture was cooled to 5° C. over a period of 2h. At an internal temperature of 35° C.–40° C., crystallization started.

The solid was filtered off with suction, washed with 100 ml of cold water and dried, giving 237 g of 4-nitro-2-sulfobenzoic acid potassium salt.

The experiment was repeated using, instead of potassium acetate, aqueous potassium hydroxide solution and potassium chloride, respectively, to precipitate the K salt.

What is claimed is:

1. A process for preparing substituted aromatic and heteroaromatic aldehydes or carboxylic acids of the formula

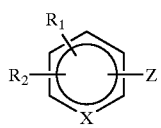

I in which $R_1$ and $R_2$ are H, $C_1$–$C_4$ alkyl, $C_1$–$C_4$ alkoxy, OH, $NO_2$, CN, COOH, $CONH_2$, COOR, $NH_2$, $SO_3H$ or halogen and R is $C_1$–$C_4$ alkyl and where $R_1$ and $R_2$ are not simultaneously H, X is C or N and Z is CHO or COOH, which comprises dissolving a corresponding symmetric stilbene compound of the formula

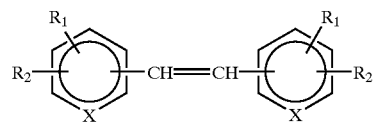

II in which $R_1$, $R_2$ and X are as defined above either directly or as a salt in water and reacting it at a temperature of from 0 to +100° C. with ozone, giving a mixture comprising the corresponding aldehyde of the formula I and hydroperoxide from which a) after acidic or alkaline decomposition of the hydroperoxide, the corresponding aldehyde of the formula I is isolated, or which b) is directly reacted, under acidic or alkaline decomposition of the hydroperoxide and with addition of an oxidizing agent, to give the corresponding carboxylic acid of the formula I or its salt, which is then isolated.

2. The process as claimed in claim 1, wherein, in the compounds of the formula I, X, $R_1$ and $R_2$ are in the o, m or p position to the substituent Z, with the proviso that, if X=N, the N atom is unsubstituted.

3. The process as claimed in claim 2, wherein, as compounds of the formula I, 2-sulfobenzoic acid, 4-nitro-2-sulfobenzoic acid, 4-nitro-2-sulfobenzaldehyde, 4-aminobenzoic acid, terephthalic acid or substituted 4-pyridinecarboxylic acid or their sodium or potassium salts are prepared.

4. The process as claimed in claim 1, wherein the compounds of the formula II are dissolved directly, in the form of their alkali metal salts of acids or in the form of a chloride, nitrate, sulfate or phosphate of basic groups, in water, giving a 1–50% strength solution.

5. The process as claimed in claim 1, wherein, for isolating the aldehyde, the mixture is adjusted to an alkaline pH, the hydroperoxide is decomposed and the aldehyde is crystallized after cooling.

6. The process as claimed in claim 5, wherein, as aldehydes of the formula I, aldehydes having $NO_2$ and/or $SO_3H$ substituents are isolated.

7. The process as claimed in claim 1, wherein, for isolating the carboxylic acids, the mixture is admixed with hydrogen peroxide, a peracid, ozone, molecular oxygen, sodium hypochlorite or sodium perborate as oxidizing agent in an amount which is at least equimolar to the amount of aldehyde present in the mixture, the hydroperoxide is, either before, after or during oxidation, subjected to acidic or alkaline decomposition and the carboxylic acid or its salt is isolated by extraction or crystallization.

8. The process as claimed in claim 7, wherein the hydroperoxide is decomposed by adding an acid.

9. The process as claimed in claim 7, wherein the carboxylic acid is crystallized as potassium salt by addition of potassium chloride, aqueous potassium hydroxide solution, potassium formate, potassium acetate or potassium carbonate.

* * * * *